United States Patent

Fahrenholz et al.

Patent Number: 5,470,948
Date of Patent: Nov. 28, 1995

[54] VASOPRESSIN AND VASOTOCIN DERIVATIVES

[75] Inventors: Falk Fahrenholz, Frankfurt am Main; Walter Elger, Berlin; Marianne Fähnrich, Berlin; Kryzsztof Chwalisz, Berlin, all of Germany

[73] Assignee: Schering Aktiengesellschaft, Berlin, Germany

[21] Appl. No.: 78,289

[22] PCT Filed: Dec. 21, 1991

[86] PCT No.: PCT/EP91/02496

§ 371 Date: Jun. 22, 1993

§ 102(e) Date: Dec. 20, 1993

[87] PCT Pub. No.: WO92/11287

PCT Pub. Date: Jul. 9, 1992

[30] Foreign Application Priority Data

Dec. 22, 1990 [DE] Germany ............ 40 42 008.6

[51] Int. Cl.⁶ .................... A61K 38/00; C07K 7/16
[52] U.S. Cl. ............................. 530/315; 530/317
[58] Field of Search ..................... 530/315, 317

[56] References Cited

U.S. PATENT DOCUMENTS 4,402,942  9/1983  Melin ..................... 514/16
4,766,108  8/1988  Ali ........................ 514/16

FOREIGN PATENT DOCUMENTS 0270371  6/1988  European Pat. Off. .
2074582  11/1981  United Kingdom .

OTHER PUBLICATIONS

F. Kaspryzkowski et al, "Synthesis, biological activity and receptor binding affinity of two [8-arginine]vasopressin analogues with inhibitory properties", *Collection Czechoslovak Chem. Commun.*, vol. 53, pp. 2907–2913 (1988).

Z. Grzonka et al, "Synthesis and some pharmacological properties of oxytocin and vasopressin analogues with sarcosine or N-methyl-L-alanine in position 7", *Journal of Medicinal Chemistry*, vol. 26, pp. 555–559 (1983).

Z. Grzonka et al, "Arginine-vasopressin analogues with high antidiuretic/vasopressor selectivity. Synthesis, biological activity, and receptor binding affinity of arginine-vasopressin analogues with substitutions in positions 1,2,4,7 and 8", *Journal of Medicinal Chemistry*, vol. 29, pp. 96–99 (1986).

C. F. Nelson et al, "The synthesis and structure-activity studies of vasopressin antagonists modified at positions one and two", *Peptides—Proceedings of the Ninth American peptide Symposium* (1987), published by C. M. Deber et al., Pierce Chemical Co., (Rockford Ill., U.S.), pp. 615–618.

*Primary Examiner*—Jill Warden
*Assistant Examiner*—P. Lynn Touzeau
*Attorney, Agent, or Firm*—Millen, White, Zelano, & Branigan

[57] ABSTRACT

This invention relates to new vasopressin and vasotocin derivatives of general formula I

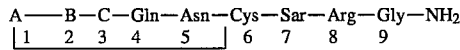

in which
  A stands for the radical Mca (=3-mercapto-3,3-cyclpentamethylenepropionyl radical) or for the radical Mpa (=3-mercaptopropionyl radical),
  B stands for the amino acid radicals D-Tyr, D-Tyr(Et), D-Phe, Tyr(OMe), D-Ile, D-Trp, or the radical of a hydrophobic D-amino acid, and
  C stands for phenylalanine (Phe; vasopressin derivatives) or isoleucine (Ile; vasotocin derivatives).
They have a high activity toward the oxytocin and the V-vasopressin receptors and can be used for the production of pharmaceutical agents.

11 Claims, No Drawings

VASOPRESSIN AND VASOTOCIN DERIVATIVES

This invention relates to new vasopressin and vasotocin derivatives of general formula I

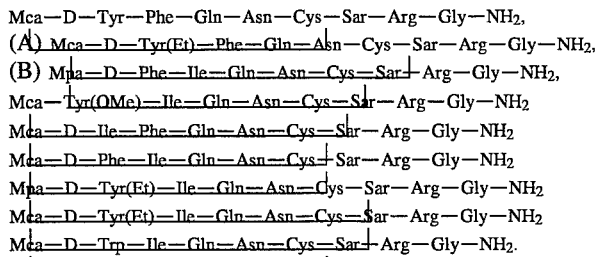

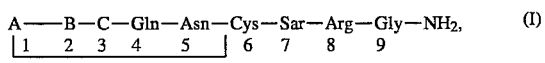

$$A\text{——}B\text{—}C\text{—}Gln\text{—}Asn\text{—}Cys\text{—}Sar\text{—}Arg\text{—}Gly\text{—}NH_2, \quad (I)$$
$$\phantom{A\text{——}}|\;1\quad 2\quad 3\quad 4\quad 5\;|\;6\quad 7\quad 8\quad 9$$

in which

A stands for the radical Mca (=3-mercapto-3,3-cyclopentamethylene-propionyl radical) or for the radical Mpa (=3-mercaptopropionyl radical), B stands for the amino acid radicals D-Tyr, D-Tyr(Et), D-Phe, Tyr(OMe), D-Ile, D-Trp or the radical of a hydrophobic D-amino acid, and C stands for phenylalanine (Phe; vasopressin derivatives) or isoleucine (Ile; vasotocin derivatives).

The new derivatives are distinguished from the natural hormone [Arg[8]]-vasopressin (AVP) by substitution of the amino acid radical Cys (cysteine) in 1-position by the radical Mca

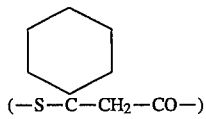

or the radical Mpa (—S—CH$_2$—CH$_2$—CO—) of the amino

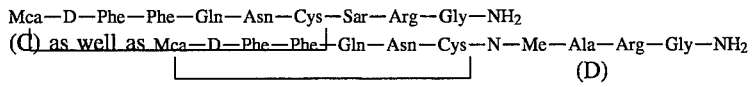

acid radical L-Tyr (L-tyrosine) in 2-position by the radical D-Tyr, D-Tyr(Et) [D-tyrosine-O-ethyl ether] or the radical of a hydrophobic D-amino acid, optionally of the amino acid radical phenylalanine (Phe) in 3-position by the radical isoleucine (Ile) as well as of the radical proline (Pro) in 7-position by the radical safcosine (Sar).

The derivatives of formula I have a high affinity to the oxytocin receptor and to V$_1$-vasopressin receptor; they have both oxytocin-antagonistic and V$_1$-vasopressin-antagonistic action. By introducing the Mca radical in 1-position of the vasopressin structure, this "reversal of the properties" of AVP is achieved. Preferred are Compounds, which represent competitive antagonists of oxytocin, are already known.

In EP-A-0 112 809, vasotocin derivatives

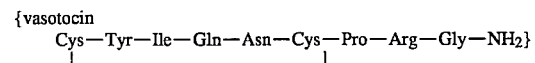

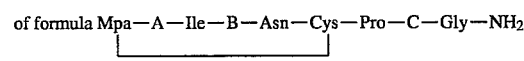

are described, in which

Mpa means the 3-mercaptopropionyl radical (—S—CH$_2$CH$_2$—CO—),

A means the amino acid radical of L- or D-tyrosine-O-ethyl ether, i.e., L- or D-Tyr(Et), B means the amino acid radical of glutamine (Gln), threonine (Thr) or valine (Val) as well as C means the amino acid radical of L- or D-arginine (Arg), ornithine (Orn) or citrulline (Cit).

The two vasopressin analogs

Mca—D—Phe—Phe—Gln—Asn—Cys—Sar—Arg—Gly—NH$_2$
(C) as well as Mca—D—Phe—Phe—Gln—Asn—Cys—N—Me—Ala—Arg—Gly—NH$_2$ (D)

stem from the Collection Czechoslovak Chem. Commun., Vol. 53, p. 2907, (1988).

Relative to these first-mentioned known compounds, the compounds according to the invention are distinguished by a substantially greater and longer reversible inhibition of the action of the oxytocin; the new compounds have no agonistic activity whatsoever.

The examination of (a) oxytocic and (b) oxytocin-inhibiting activity took place by continuous tonometry of the uterus of pregnant guinea pigs on d 40±1 p.c.:

24 hours before the examination, a microballoon, which is filled with water, was implanted in the uterus. The balloon is connected by a catheter with a pressure sensor. An i.v. catheter simultaneously was inserted in the jugular vein. After an adaption phase of about 30 minutes to 1 hour, the oxytocin antagonist was examined for agonistic [see (a)] and antagonistic activity [see (b)]. Both oxytocin and the test substance were administered intravenously (vehicle: 0.9% common salt solution).

(a) Agonistic activity:
0.1 µg, 1.0 µg, 10.0 µg and 100.0 µg/ml/animal (B) i.v.
(b) Antagonistic activity:
1. 100.0 µg/ml/animal (B) i.v.+15 min later 30 mU/ml of oxytocin i.v.
Complete inhibition of the oxytocin action
2. 100.0 µg/ml/animal (B) i.v.+15 min later 100 mU/ml of oxytocin i.v.

1 hour after the last administration of (B), a recovery of the uterus takes place, i.e., clear contractions occur again.
When Mpa—D—Tyr(Et)—Ile—Thr—Asn—Cys—Pro—Orn—Gly—NH$_2$
|_____|

(E) (Compound of example 11 of EP-A-0 112 809) is administered according to the same dosage patterns, the duration and strength of the uterus contraction activity are only weakened.

Compound (B) according to the invention is comparable in the described model to compound (C) relative to the oxytocin-antagonistic action.

Because of their oxytocin-antagonistic action, the compounds according to the invention can be used to produce pharmaceutical preparations.

Oxytocin antagonists inhibit the uterus motor response by a direct action on the myometrium and indirectly by the inhibition of the uterine (decidual) prostaglandin synthesis. They are therefore suitable for treatment and prophylaxis of premature labor (premature delivery, impending miscarriage) and dysmenorrheic symptoms.

In addition to the posterior lobe of the pituitary gland, the ovary or the corpus luteum secretes oxytocin. If the latter action takes place in the uterus, the above-discussed aspects apply. In the ovary itself, oxytocin controls certain functions of the corpus luteum. The inhibition of these functions, depending on dose and phase of the cycle, can lead to an increase or inhibition of the luteal hormone production. Correspondingly, the life span of the corpus luteum can also be shortened or extended. Corpus luteum insufficiency therefore represents another potential indication for the compounds according to the invention.

For the treatment of premature delivery (premature labor), mainly betamimetics have thus far been used. The problem of this treatment consists in the fact that an organ specificity does not exist and the substances are loaded with a broad spectrum of considerable side effects.

For the treatment of dysmenorrheic symptoms, mainly analgesics and antiinflammatory substances (acetylsalicylic acid, i.a.) have thus far been used. The latter substance class inhibits the prostaglandin synthesis in the uterus and thus results in reducing the increased uterus motor response. The organ specificity is not assured either.

Since the action of oxytocin is largely uterus-specific and it acts directly on the myometrium stimulating labor, competitive oxytocin antagonists, in the treatment and prophylaxis of premature labor, should display their action only on the target organ.

A possible increase of blood pressure during the treatment with the oxytocin antagonist is itself inhibited by the latter by its vasopressin-antagonistic partial action (vasopressin receptors are both in the uterus and at other points in the body). This damping action on the blood pressure is only important in pathological situations; a reduction of the normal blood pressure by administration of the compounds according to the invention in doses, in which the oxytocin-antagonistic action occurs, is not observed. The compounds according to the invention have a relatively long-term vasopressin-antagonistic action. Vasopressin receptors were also noted in the myometrium and decidua (Guillon, G. et al., 3. Clin. Endocrinol. Metab. 1987, 64:1129; Ivanisevic, M. et al., Am. J. Obstet. Gynecol. 1989, 161:1637). There are also indications (Akerlund, M., Acta. Obstet. Gynecol. Scand. 66, 5:459) that vasopressin plays an important role in the pathogenesis of dysmenorrheic symptoms. In this connection, the vasopressin-antagonistic partial action of the compounds according to the invention appears advantageous.

The compounds according to the invention can be processed in a way usual in the art with pharmaceutically compatible auxiliary agents and/or diluents to pharmaceutical preparations. Preferably, they are administered—dissolved in physiological common salt solution—by injection, infusion or intranasal administration.

The production of the vasopressin derivatives according to the invention can take place analogously to processes known in the field of peptide chemistry. Suitably, the so-called "solid-phase peptide synthesis" is used [Merrifield, R. B., J. Am. Chem. Soc. 85, 2149 (1963); Merrifield, R. B., Biochemistry 3, 1385 (1964); Manning, M., J. Am. Chem. Soc. 90, 1348 (1968)] in a recently described variant [Grzonka, Z. et al., J. Med. Chem., 26, 555 (1983)].

After the successive synthesis of the protected peptide intermediate products, the latter are cleaved off by ammonolysis of the carrier resin. To protect the amino group, the tert-butoxycarbonyl(BOC) group is used, which is again removed by treatment with 50% trifluoroacetic acid (TFA) in methylene chloride (DCM). The coupling is carried out with dicyclohexylcarbodiimide (DCCI)—in the case of some amino acids while adding N-hydroxybenzotriazole (HDBT)—or with p-nitrophenyl esters in the case of asparaginyl and glutamine radicals. The completeness of each coupling step is tracked by the Kaiser test [Kaiser, E. et al., Anal. Biochem. 34, 595 (1970)]. Protecting groups are removed from protected peptides with sodium in liquid ammonia and the formed dithiols are cyclized oxidatively with $K_3[Fe(CN)_6]$. The end products are purified by gel chromatography on Sephadex G-15.

EXAMPLES

Mobile buffer for high-pressure liquid chromatography (HPLC)

Buffer A: 0.09% trifluoroacetic acid in water
Buffer B: 0 09% trifluoroacetic acid; 9.91% water; 90% acetonitrile Thin-layer chromatography Mobile solvent systems:
BAW=n-butanol/acetic acid/water 4:1:1
CM=CHCl$_3$/CH$_3$OH 7:3
BPAW=n-butanol/pyridine/acetic acid/water 15:10:3:3
EBAW=ethyl acetate/n-butanol/acetic acid/water 1:1:1:1

BAWo=n-butanol/acetic acid/water 4:1:5, upper phase

Slabs for thin-layer chromatography:

Merck instant TLC plates of silica gel 60 $F_{254}$ (Merck, Darmstadt)

A. Reagents necessary for solid-phase synthesis:

Dichloromethane (DCM)
dimethyl formamide (DMF), freshly distilled ethanol
1:1 trifluoroacetic acid (TFA)/DCM
10% diisopropylethylamine (DIEA), freshly distilled in DCM
DCCI (MW 206.33), solution 1 M in DCM
HOBt (MW 135.13; contains about 20% $H_2O \Rightarrow$ MW 160)

The resin loaded with the first amino acid is presoaked overnight in dichloromethane before the start of the synthesis cycles.

Depending on the amino acid to be coupled, different combinations of coupling reagent and solvent are selected:

| DCCI in DCM: | DCCI + HOBt in DMF: | DCCI + HOBt in DMF/DCM 1:1 |
|---|---|---|
| BOC-Cys(Bzl)-OH | BOC-Tyr(Bzl)-OH | BOC-Arg(Tos)-OH |
| BOC-Ile-OH | BOC-Tyr(Me)-OH | |
| BOC-Lys(Tos)-OH | BOC-DTyr(MeOBzl)-O | HOBt in DMF: |
| BOC-Orn(Z)-OH | BOC-DTyr(Et)-OH | BOC-Asn-ONp |
| BOC-Phe-OH | Mca(Bzl)-OH | BOC-Gln-ONp |
| BOC-Pro-OH | Mca(MeOBzl)-OH | |
| BOC-Sar-OH | Mpa(Bzl)-OH | |
| BOC-Thr(Bzl)-OH | | |
| Z-Cys(Bzl)-OH | | |

The following three standard synthesis cycles were used:

1.) Coupling of the BOC-amino acid with DCCI as condensation reagent in DCM

Cleaving of BOC:

TFA/DCM 1:1, 5 min+25 min
3×3 min of washing with DCM

Neutralizing:

10% DIEA in DCM, 5 min+10 min 3×3 min of washing with DCM

Coupling:

4 eq of BOC-AS-OH in DCM, 10 min of equilibration
4 eq of DCCI, 1M in DCM, 4 hours of reaction time
3×3 min of washing with DCM
3×3 min of washing with EtOH
3×3 min of washing with DCM Kaiser test:

control, whether coupling is complete.

2.) Coupling of the BOC amino acid with DCCI and HOBt as an additive in DMF

Cleaving of BOC:

TFA/DCM 1:1, 5 min+25 min
3×3 min of washing with DCM

Neutralizing:

10% DIEA in DCM, 5 min+10 min
3×3 min of washing with DCM
3 min of washing with DCM/DMF 1:1
3×3 min of washing with DMF Coupling:

4 eq of BOC-AS-OH with 8 eq of HOBt in DMF, 10 min of equilibration
4 eq of DCCI, 1M in DCM, 4 hours of reaction time
3×3 min of washing with DMF
3 min of washing with DMF/DCM 1:1
3×3 min of washing with DCM
3×3 min of washing of EtOH
3×3 min of washing with DCM Kaiser test:

control whether coupling is complete.

3. Coupling of BOC-amino acid-nitrophenylester with HOBt in DMF

Cleaving of BOC:

TFA/DCM 1:1, 5 min+25 min
3×3 min of washing with DCM

Neutralizing:

10% DIEA in DCM, 5 min+10 min
3×3 min of washing with DCM
3 min of washing with DCM/DMF 1:1
3×3 min of washing with DMF Coupling:

4 eq of BOC-AS-OH with 8 eq of HOBt in DMF, 4 hours of reaction time
3×3 min of washing with DMF
3 min of washing with DMF/DCM 1:1
3×3 min of washing with DCM
3×3 min of washing with EtOH
3×3 min of washing with DCM Kaiser test:

Control whether coupling is complete.

After completion of the last coupling step to link the N-terminal amino acid, the resin from the reaction vessel is transferred to a G3 frit and washed with 3×DMF, 3×DCM, 3×$Et_2O$. Then, it is suctioned to dryness and dried on $P_2O_5$ in a vacuum desiccator.

Conversion control in the solid-phase synthesis—Kaiser test

For control, whether the individual coupling steps of the solid-phase synthesis have been completed, the ninhydrin color test (Kaiser test) introduced by E. Kaiser in the peptide synthesis is used (E. Kaiser, R. L. Colescott, C. D. Bossinger, P. I. Cook: Color test for detection of free terminal amino groups in the solid-phase synthesis of peptides, Anal. Biochem. 34, p. 595 (1970)).

B. General operating instructions

1.) Cleavage of resin—ammonolysis

The completely synthesized peptide sequence is cleaved ammonolytically from the polymer vehicle after completion of the solid-phase synthesis.

For this purpose, the resin is suspended in a new 250 ml one-necked round-bottom flask in dry methanol (20 ml per gram of resin). The suspension is cooled on a cold bath (methanol/dry ice), $NH_3$ gas dried by KOH is condensed by a gas-entry tube, until methanol and liquid ammonia are present in approximately equal amounts. Then, the gas-entry tube is removed and the flask is closed as tightly as possible with a plastic stopper (glue with a fabric adhesive tape). The reaction mixture is slowly brought to room temperature. After 48 hours of stirring at room temperature, the flask is again cooled on the cold bath, the stopper is carefully removed and the ammonia drawn off in a water jet vacuum. The suspension is then brought to dryness on a rotary evaporator. The residue is taken up in 20 ml of hot DMF and suctioned off by a G3 frit in 1000 ml of boiling hot water. The fully protected nonapeptide amide dissolved in DMF precipitates It is allowed to settle overnight at 4° C. the precipitate is filtered off by a G4 frit and washed with water. The precipitate is dried by $P_2O_5$ in a vacuum desiccator and weighed.

The remaining resin is washed with DMF, DCM and $Et_2O$, dried and weighed.

The fully protected nonapeptide amide is reprecipitated from DMF with ethanol/diethyl ether, the uniformity of the product is examined by thin-layer chromatography.

2.) Cleavage of the constant protecting groups

For the reduction, first about 500 ml of ammonia on a cold bath (methanol/dry ice) is condensed in a 1000 ml two-necked flask. It is mixed with sodium chips. The thus dried liquid ammonia is now overdistilled by careful heating on a heating mushroom in a 1000 ml three-necked flask cooled on the cold bath. About 300 ml of liquid ammonia is required for 100 mg of fully protected nonapeptide amide. If sufficient ammonia is condensed, the cold bath is removed. It is allowed to heat slowly and the fully protected nonapeptide amide is added when the ammonia begins to boil, which immediately dissolves.

In this solution, a pipette filled with solid metallic sodium is now immersed at short intervals, until a clear blue coloring lasts for more than 20 seconds in the solution. The sodium excess is immediately destroyed by instilling concentrated acetic acid. The ammonia is now drawn off in a water jet vacuum, for this purpose the flask can be slightly heated in an acetone bath (up to −30° C. bath temperature). The flask with the remaining solid residue (linear peptide amide from which the protection has been removed) is aerated with nitrogen, the cyclization to the disulfide immediately follows.

3.) Cyclization to disulfide

Subsequent to the cleavage of the constant protecting groups, the oxidative linking of the disulfide bridge between the sulfhydryl groups of the amino acid side chains in 1-position and 6-position takes place with potassium-hexacyanoferrate(III) ("red potassium prussiate") in aqueous solution.

The residue remaining after the removal of the protection is dissolved for this purpose in 1000 ml of cold 0.2 N acetic acid gassed with nitrogen. In the case of poorly soluble derivatives (antagonists with hydrophobic amino acid side chains), it can also be dissolved first in 20% acetic acid; it is then diluted with dist. water to 0.2 N. It is allowed to heat to room temperature and stirred under a nitrogen atmosphere, until all is dissolved.

The concentration of linear peptide in the cyclization should be about $10^{-4}M$, thus the intramolecular reaction (formation of an intrachenar disulfide bridge) is more probable than the intermolecular one (formation of dimers and higher oligomers).

The pH is adjusted to 7.0 to 7.5 with diluted ammonia solution. 0.01 M of potassium-hexacyanoferrate(III) solution is allowed to be instilled from a burette by drops until the solution remains weakly yellow. Another 2 ml of potassium hexacyanoferrate(III) solution is added and allowed to stir for 10 to 20 minutes.

To separate excess hexacyanoferrate(III) and hexacyanoferrate(II) ions, about 20 g of AG2-X8 anion exchange resin (chloride form) is added and stirred with the solution for 30 minutes. The contents of the flask are filtered by additional AG2-X8 anion exchange resin on a G3 frit, the resin is washed with 0.2 N AcOH, then with 20% AcOH, the filtrate is distributed to 4 flasks and freeze-dried. The lyophilizates are dissolved in diluted acetic acid, combined and freeze-dried twice more.

4.) Purification

The cyclized peptides are subjected to two steps of gel chromatography for desalting and purification:

1.) Gel chromatography on Sephadex-G15 with 50% acetic acid as eluent. The lyophilizate after cyclization is dissolved in a maximum of 20 ml of 50% AcOH and applied to the column (length 166 cm, φ4.5 cm). A constant flow rate of 20 ml/hour is selected by a peristaltic pump. It is fractionated in 20 minute steps, the UV absorption of the eluate is measured by a flow photometer at 276 nm and recorded on a flat-bed recorder. The fractions are controlled by HPLC, equal fractions are combined and freeze-dried.

2.) Gel chromatography on Sephadex-G15 with 0.2 N of acetic acid as eluent. The main fraction from the first gel chromatography is dissolved in a little 0.2 N acetic acid and applied to the column (length 180 cm, φ2 cm). A flow rate of 10 ml/hour is selected by the peristaltic pump. It is fractionated in 20 minute steps and the UV absorption of the eluate is recorded at 276 nm, the fractions are controlled by HPLC, equal fractions are combined and freeze-dried several times.

After the purification by gel chromatography, occasionally weakly yellow-colored products are obtained, which also can contain up to 20% salts. The salt content of a weighed sample can be determined by measuring the absorbency at 276 nm (=tyrosine absorption). Further desalting can be achieved by a SEP-PAK cartridge. The peptide (up to 30 mg) is dissolved in diluted acetic acid and applied on a SEP-PAK $C_{18}$ cartridge. It is first eluted with water, then stepwise in increasing concentrations with acetonitrile in water, finally with pure acetonitrile. The fractions are controlled by HPLC, the product fraction is freeze-dried. The pure product is obtained in the form of white flakes. I) Synthesis of [Mca$^1$, D-Tyr$^2$, Sar$^7$]AVP (A)

1.) Solid-phase synthesis

Synthesis diagram for solid-phase synthesis of Mca(MeOBzl)-DTyr(MeOBzl)-Phe-Gln-Asn-Cys(Bzl)-Sar-Arg(Tos)-Gly-O-<MF> (according to the general operating instructions under A.1.)–3.))

| Batch: 1.50 g of BOC-Gly-O-<MF> = 1.20 mmol | | |
|---|---|---|
| Amino acid derivative | Coupling condition | Remarks/Kaiser test (n = negative) |
| BOC-Arg(Tos)-OH × 0.25 H$_2$O MW 428.51 6 mmol = 2.57 g | 6 mmol of DCCI 12 mmol of HOBt 3.5 h in DCM/DMF 1:1 | n |
| BOC-Sar-OH MW 189.20 6 mmol = 1.14 g | 6 mmol of DCCI 16.5 h in DCM | n |
| BOC-Cys(Bzl)-OH MW 311.40 6 mmol = 1.87 g | 6 mmol of DCCI 5 h in DCM | n |
| BOC-Asn-ONp MW 353.33 6 mmol = 2.12 g | 12 mmol of HOBt 14 h in DMF | n |
| BOC-Gln-ONp MW 367.36 6 mmol = 2.20 g | 12 mmol of HOBt 16 h in DMF | n |
| BOC-Phe-OH MW 265.31 6 mmol = 1.59 g | 6 mmol of DCCI 2 h in DCM | Kaiser test remains positive => subsequent coupling even after repeated washing |
| 3 mmol = 0.80 g | 3 mmol of DCCI 2 h in DCM | n |

After the coupling, the resin is transferred from BOC-Phe-OH to a G4 frit, washed with DMF, DCM and Et$_2$O and suctioned to dryness.

Weight after drying of the resin on P$_2$O$_5$: 2.75 g.

The solid-phase synthesis of [Mca$^1$, DTyr(Et)$^2$, Sar$^7$]AVP (B) is performed with one part of the heptapeptide resin (see section II), the solid-phase synthesis of [Mca$^1$, DTyr$^2$, Sar$^7$]AVP (A) is continued with the other part;

0.8 g (about 0.4 mmol) of BOC-Phe-Gln-Asn-Cys(Bzl)-Sar-Arg(Tos)-Gly-O-<MF> resin is soaked in DCM overnight to continue the solid-phase synthesis.

| Amino acid derivative | Coupling condition | Remarks/Kaiser test (n = negative) |
|---|---|---|
| BOC-DTyr(MeOBzl)-OH MW 401.45 mmol = 1.20 g | 3 mmol of DCCI 6 mmol of HOBt 16 h in DMF | Kaiser test also after multiple washing with DMF positive => post-coupling |
| mmol = 0.40 g | 1 mmol of DCCI 2 mmol of HOBt 15 h in DMF | n |
| Mca(Bzl)-OH MW 264.38 3 mmol = 0.79 g | 3 mmol of DCCI 6 mmol of HOBt 16 h in DMF | Kaiser test also after multiple washing with DMF positive => post-coupling |
| 2 mmol = 0.53 g | 2 mmol of DCCI 4 mmol of HOBt 16 h in DMF | Kaiser test also after multiple washing with DMF positive => 2nd post-coupling |
| 1 mmol = 0.26 g | 1 mmol of DCCI 2 mmol of HOBt 4 h in DMF | n |

Weight after washing the resin with DMF, DCM, Et$_2$O and drying on P$_2$O$_5$: 0.93 g

2.) Ammonolysis of the peptide resin

The peptide resin from the solid-phase synthesis is subjected to the ammonolytic cleavage according to general operating instructions (section B.1.). The reaction flask is stirred for 48 hours at room temperature.

3.) Yield and analytical data of the fully protected nonapeptide amide 0.35 g = 0.22 mmol of fully protected nonapeptide amide is obtained. Relative to the amount of BOC-Phe-Gln-Asn-Cys(Bzl)-Sar-Arg(Tos)-Gly-O-<MF> used, this corresponds to a yield of 55%. Mca(Bzl)-DTyr(MeOBzl)-Phe-Gln-Asn-Cys(Bzl)-Sar-Arg(Tos)-Gly-NH$_2$ Empirical formula: C$_{78}$H$_{98}$N$_{14}$O$_{15}$S$_3$ Molecular weight: 1567.14

\* Thin-layer chromatograms

R$_{f(BAW)}$=0.73
R$_f$(CM)=0.62

\* HPLC

System (b):

gradient 50–90% B, 15 min. retention time t$_R$=9.0 min., k'=3.5

4.) Cleavage of the constant protecting groups and cyclization

Batch: 154 mg of Mca(Bzl)-DTyr(MeoBzl)-Phe-Gln-Asn-Cys(Bzl)-Sar-Arg(Tos)-Gly-NH$_2$ (MW 1567.14) = 0.1 mmol The cleavage of the constant protecting groups with sodium in liquid ammonia is performed according to the general operating instructions (section B.2.). After removal of the ammonia, the residue is dissolved in 1000 ml of 0.2 N acetic acid (poorly soluble!). A little sticky residue remains on the vessel wall. The pH is adjusted with diluted ammonia solution to 7.1.

For cyclization, 30 ml of a 5 mmol K$_3$[Fe(CN)$_6$] solution is required until permanent yellow coloring of the reaction solution. This corresponds to 0.15 mmol and thus 75% of the calculated amount. Altogether, 35 ml of 5 mmol of K$_3$[Fe(CN)$_6$] solution is added. The reaction solution is treated with anion exchange resin and freeze-dried several times.

5.) Purification

The crude product is taken up in 40 ml of 50% acetic acid and subjected to a gel chromatography on Sephadex-G15.
Column: 166×4.5 cm

11

Flow rate: 20 ml/hour

Eluent: 50% acetic acid 3 fractions/hour

The fractions are examined by HPLC.

Elution of the main product: fractions 132–150 after 44 to 50 hours elution volume 880–1000 ml.

For further desalting, the product is dissolved in 10 ml of aqueous acetic acid (pH=3), fed to a SEP-PAK $C_{18}$ cartridge, washed with 10 ml of water and eluted with 10 ml of 60% acetonitrile in water.

The eluate is freeze-dried twice.

6.) Yield and analytical data 68 mg=0 061 mmol of pure [$Mca^1$, $D\text{-}Tyr^2$, $Sar^7$]AVP is obtained in the form of white flakes.

Relative to the fully protected nonapeptide amide used for reductive removal of protection, this corresponds to a yield of 61%.

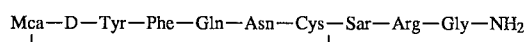

Empirical formula: $C_{49}H_{70}N_{14}O_{12}S_2$ Molecular weight: 1111.30

* Thin-layer chromatograms:

$R_f(BAW)=0.29$ $R_f(BPAW)=0.44$

* HPLC:

System (b):

gradient 20–80% B against A, 60 minutes retention time $t_R$=15.5 min., k'=6.8

* FAB-mass spectrum:

Molpeak $MH^+$=1111 theoretically calculated: 1110.47

* UV spectrum:

absorption maxima at λ=225 nm (n, π*-transition of the carbonyl function of the peptide bonds) and λ=278 nm (π,π*-transition in the aromatic system of tyrosine)

* Amino acid analysis:

Phe 0.96; DTyr 0.52; Gln 0.99; Asn 1.00; Arg 1.01; Gly 1.01 (Mca,Cys and Sar were not determined)

II) Synthesis of [$Mca^1$, $D\text{-}Tyr(Et)^2$, $Sar^7$]AVP (B)

1.) The synthesis begins with the heptapeptide resin BOC-Phe-Gln-Asn-Cys(Bzl)-Sar-Arg(Tos)-Gly-O-<MF> from the solid-phase synthesis of [$Mca^1$, $D\text{-}Tyr^2$, $Sar^7$]-AVP (A).

0.8 g (about 0.4 mmol) of heptapeptide resin is soaked overnight in DCM.

| Amino acid derivative | Coupling condition | Remarks/Kaiser test (n = negative) |
|---|---|---|
| BOC-DTyr(Et)-OH MW 325.36 | 1.5 mmol of DCCI 3 mmol of HOBt | Kaiser test also after multiple |

12

| Amino acid derivative | Coupling condition | Remarks/Kaiser test (n = negative) |
|---|---|---|
| 1.5 mmol = 0.49 g | 16 h in DMF | washing with DMF positive => post-coupling |
| 1 mmol = 0.33 | 1 mmol of DCCI 2 mmol of HOBt 15 h in DMF | n |
| Mca(Bzl)-OH MW 264.38 3 mmol = 0.79 g | 2 mmol of DCCI 4 mmol of HOBt 15 h in DMF | Kaiser test also after multiple washing with DMF positive => post-coupling |
| 2 mmol = 0.53 g | 2 mmol of DCCI 4 mmol of HOBt 16 h in DMF | Kaiser test also after multiple washing with DMF positive => 2nd post-coupling |
| 1 mmol = 0.26 g | 1 mmol of DCCI 2 mmol of HOBt 3 h in DMF | n |

Weight after washing the resin with DMF, DCM, $Et_2O$ and drying on $P_2O_5$ in a vacuum desiccator: 0.9 g 2.) Ammonolysis of the peptide resin The peptide resin from the solid-phase synthesis is subjected to the ammonolytic cleavage according to the general operating instructions (section B.1.). The reaction flask is stirred for 48 hours at room temperature.

3.) Yield and analytical data of the fully protected nonapeptide amide 0.35 g=0.24 mmol of fully protected nonapeptide amide is obtained. Relative to the amount of BOC-Phe-Gln-Asn-Cys(Bzl)-Sar-Arg(Tos)-Gly-O-<MF> used, this corresponds to a yield of 60%. Mca(Bzl)-DTyr(Et)-Phe-Gln-Asn-Cys-(Bzl)-Sar-Arg(Tos)-Gly-$NH_2$ Empirical formula: $C_{72}H_{94}N_{14}O_{14}S_3$ Molecular weight: 1475.80

* Thin-layer chromatograms $R_f(BAW)=0.72$ $R_f(CM)=0.61$

* HPLC

System (b):

gradient 50–90% B, 15 min retention time $t_R$=7.24 min., k'=2.6

4.) Cleavage of the constant protecting groups and cyclization

Batch: 140 mg of Mca(Bzl)-DTyr(Et)-Phe-Gln-Asn-Cys-(Bzl)-Sar-Arg(Tos)-Gly-$NH_2$ (MW 1475.80)=0.095 mmol The cleavage of the constant protecting groups with sodium in liquid ammonia is performed according to the general operating instructions (section B.2.).

After removal of the ammonia, the residue is dissolved in 1000 ml of 0.2 N acetic acid (poorly soluble, the solution is slightly opalescent). The pH is adjusted with diluted ammonia solution to 7.2.

For cyclization, 33 ml of a 5 mmol $K_3[Fe(CN)_6]$ solution is required until permanent yellow coloring of the reaction solution. This corresponds to 0.165 mmol and thus 87% of the calculated amount. Altogether, 53 ml of 5 mmol of $K_3[Fe(CN)_6]$ solution is added. The reaction solution is treated with anion exchange resin and freeze-dried several times.

5.) Purification

The crude product is taken up in 40 ml of 50% acetic acid and subjected to a first step of gel chromatography on Sephadex-G15.

Column: 166×4.5 cm

Flow rate: 20 ml/hour

Eluent: 50% acetic acid 3 fractions/hour

The fractions are examined by HPLC.

Elution of the main product: Fractions 125–129 after 42 to 43 hours elution volume 830–860 ml.

For further desalting of the product, it is dissolved in 10 ml of aqueous acetic acid (pH=3) and fed to a SEP-PAK $C_{18}$ cartridge. It is washed with water and eluted with 60% acetonitrile in water. The eluate is freeze-dried twice; 26 mg of pure product is obtained.

Fractions 121–124 and 130–140 of the gel chromatography, which contain slight impurities, are combined, freeze-dried and subjected to a second step of gel chromatography.

Column: 180×2 cm

Flow rate: 10.0 ml/hour

Eluent: 0.2 N acetic acid 3 fractions/hour

The fractions are examined by HPLC.

Elution of the main product: Fractions 126–135 after 42 to 45 hours elution volume 420–450 ml.

The main product is subjected to another desalting by a SEP-PAK $C_{18}$ cartridge (as above), 9.5 mg of pure product is obtained.

6.) Yield and analytical data

A total of 35 5 mg=0 031 mmol of pure [$Mca^1$, D-Tyr$(Et)^2$, $Sar^7$]AVP is obtained in the form of white flakes. Relative to the fully protected nonapeptide amide used for reductive removal of the protection, this corresponds to a yield of 33%.

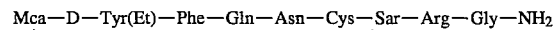

Empirical formula: $C_{51}H_{74}N_{14}O_{12}S_2$ Molecular weight: 1139.35

\* Thin-layer chromatograms:

$R_f(BAW)=0.29$ $R_f(BPAW)=0.49$

\* HPLC:

System (b):

gradient 20–80% B against A, 60 minutes retention time $t_R$=24.4 min., k'=11.2

\* FAB-mass spectrum: Molpeak $MH^+$=1139 theoretically calculated: 1138.51

\* UV spectrum:

absorption maxima at $\lambda$=230 nm (n,$\pi$\*-transition of the carbonyl function of the peptide bonds) and $\lambda$=281 nm ($\pi,\pi$,-transition in the aromatic system of tyrosine)

\* Amino acid analysis:

Phe 0.78; Gln 0.87; Asn 1.00; Arg 0.99; Gly 0.96 (Mca, DTyr(Et), Cys and Sar were not determined)

Completely analogously to the production of the two above-mentioned compounds described in detail, the following additional compounds of general formula I are obtained by using the corresponding BOC-protected amino acids. For synthesis of the derivatives, which are to contain the Mpa radical in 1-position, instead of Mca-(Bzl)-OH) in the last coupling step, Mpa-(Bzl)-OH) is used as reaction partner. The compounds are characterized by the molpeak in the FAB mass spectrum (MH+), which corresponds in each case to the theoretical calculations.

|  | Molpeak MH+ |
|---|---|
| Mpa—D—Phe—Ile—Gln—Asn—Cys—Sar—Arg—Gly—NH₂ | 933.5 |
| Mca—Tyr(OMe)—Ile—Gln—Asn—Cys—Sar—Arg—Gly—NH₂ | 1091.8 |
| Mca—D—Ile—Phe—Gln—Asn—Cys—Sar—Arg—Gly—NH₂ | 1062.0 |
| Mca—D—Phe—Ile—Gln—Asn—Cys—Sar—Arg—Gly—NH₂ | 1061.5 |

| | Molpeak MH+ |
|---|---|
| Mpa—D—Tyr(Et)—Ile—Gln—Asn—Cys—Sar—Arg—Gly—NH₂ 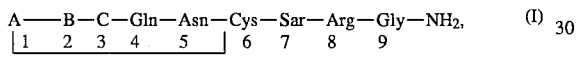 | 1037.2 |
| Mca—D—Tyr(Et)—Ile—Gln—Asn—Cys—Sar—Arg—Gly—NH₂ | 1105.6 |
| Mca—D—Trp—Ile—Gln—Asn—Cys—Sar—Arg—Gly—NH₂ | 1100.4 |

An example for the production of a pharmaceutical composition containing a compound according to the invention:

0.5 mg of the vasopressin derivative is dissolved with 5 mg of mannitol in distilled water. This solution is filled in an ampoule, which is closed and freeze-dried. In the case of storage under freeze-drying conditions, the contents of the ampoule can be removed in portions and then diluted with isotonic common salt solution to a concentration suitable for use.

We claim:

1. A vasopressin or vasotocin derivative of formula I $$A\text{——}B-C-Gln-Asn-Cys-Sar-Arg-Gly-NH_2, \quad (I)$$
$$\phantom{A\text{——}B-C-}1\phantom{-}2\phantom{-}3\phantom{-}4\phantom{-}5\phantom{-}6\phantom{-}7\phantom{-}8\phantom{-}9$$

wherein

A is a 3-mercapto-3,3-cyclopentamethylene-propionyl radical (Mca) or a 3-mercapto-propionyl radical (Mpa), B is an amino acid radical D-Tyr, D-Tyr(Et), D-Phe, Tyr(OMe), D-Ile, D-Trp or a radical of a hydrophobic D-amino acid, and C is Phe (vasopressin derivative) or Ile (vasotocin derivative), with the proviso that B is not D-Phe when C is Phe.

2. A vasopressin or vasotocin derivative of formula I, which is

Mca—D—Tyr—Phe—Gln—Asn—Cys—Sar—Arg—Gly—NH₂, 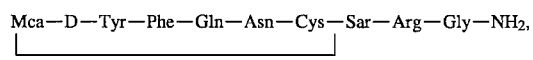

Mca—D—Tyr(Et)—Phe—Gln—Asn—Cys—Sar—Arg—Gly—NH₂, 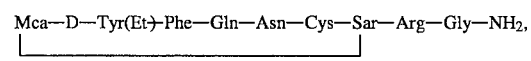

MPa—D—Phe—Ile—Gln—Asn—Cys—Sar—Arg—Gly—NH₂, 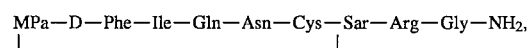

Mca—Tyr(OMe)—Ile—Gln—Asn—Cys—Sar—Arg—Gly—NH₂, 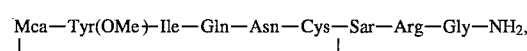

Mca—D—Ile—Phe—Gln—Asn—Cys—Sar—Arg—Gly—NH₂, 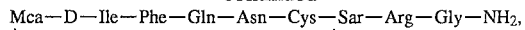

Mca—D—Phe—Ile—Gln—Asn—Cys—Sar—Arg—Gly—NH₂, 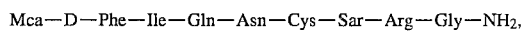

Mpa—D—Tyr(Et)—Ile—Gln—Asn—Cys—Sar—Arg—Gly—NH₂, 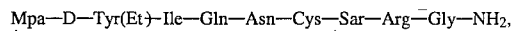

Mca—D—Tyr(Et)—Ile—Gln—Asn—Cys—Sar—Arg—Gly—NH₂, 

or

Mca—D—Trp—Ile—Gln—Asn—Cys—Sar—Arg—Gly—NH₂. 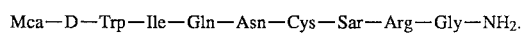

3. A pharmaceutical preparation, comprising a compound of claim 1 and a pharmaceutically acceptable excipient.

4. A pharmaceutical preparation of claim 1, in an intravenously administrable form.

5. A method of treating premature labor, including premature delivery and impending miscarriage, comprising administering to a patient in need of such treatment an effective amount of a compound of claim 1.

6. A method of treating symptoms of dysmenorrhea, comprising administering to a patient in need of such treatment an effective amount of a compound of claim 1.

7. A method of treating corpus luteum insufficiency, comprising administering to a patient in need of such treatment an effective amount of a compound of claim 1.

8. A pharmaceutical preparation of claim 4, wherein the excipient is a physiological common salt solution.

9. A method of treating premature labor, including premature delivery and impending miscarriage, comprising administering to a patient in need of such treatment an effective amount of a pharmaceutical preparation of claim 4.

10. A method of treating symptoms of dysmenorrhea, comprising administering to a patient in need of such treatment an effective amount of a pharmaceutical preparation of claim 4.

11. A method of treating corpus luteum insufficiency, comprising administering to a patient in need of such treatment an effective amount of a pharmaceutical preparation of claim 4.

* * * * *